Figure 1A:
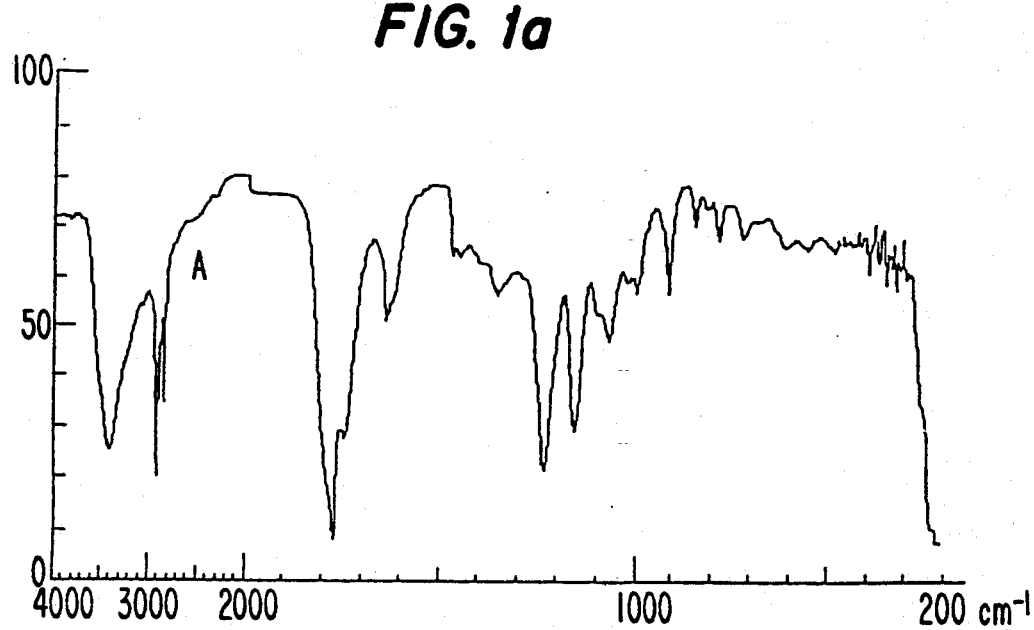
Figure 1B:
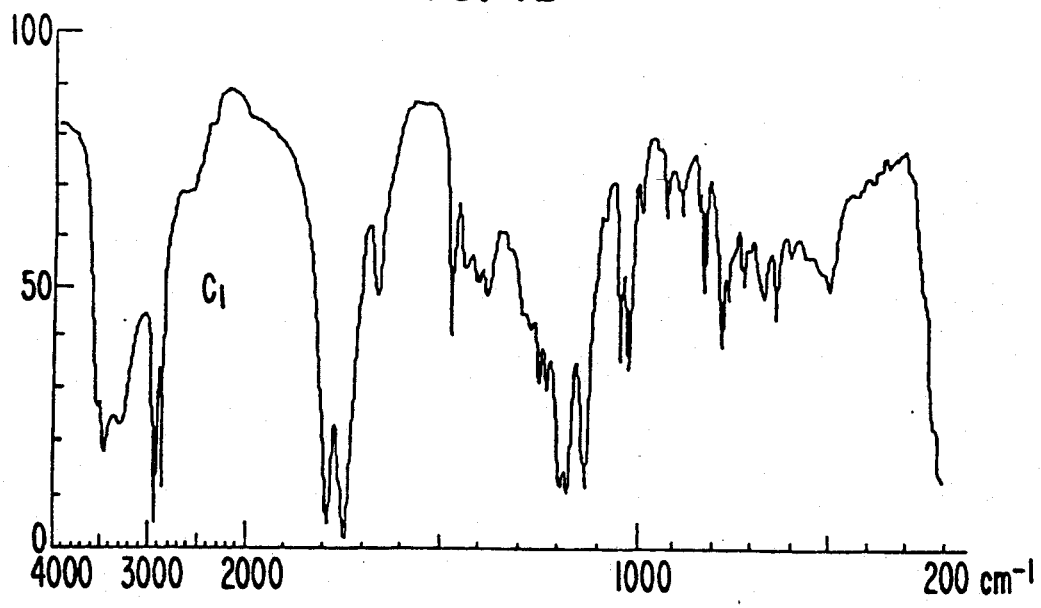
Figure 2A:
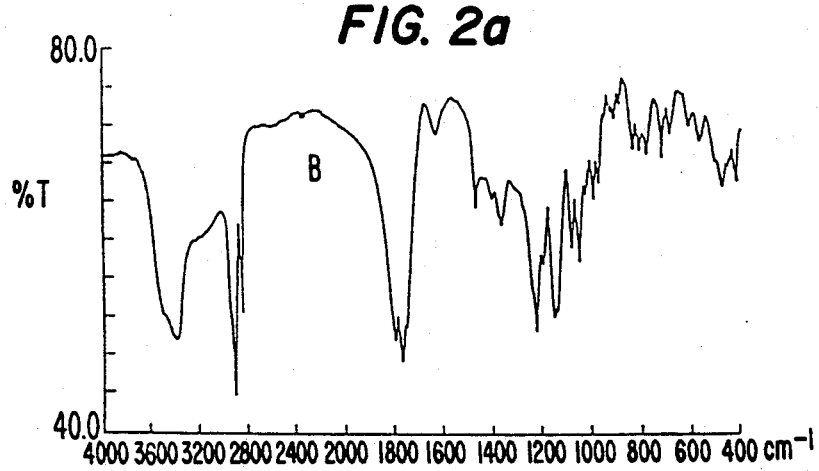
Figure 2B:
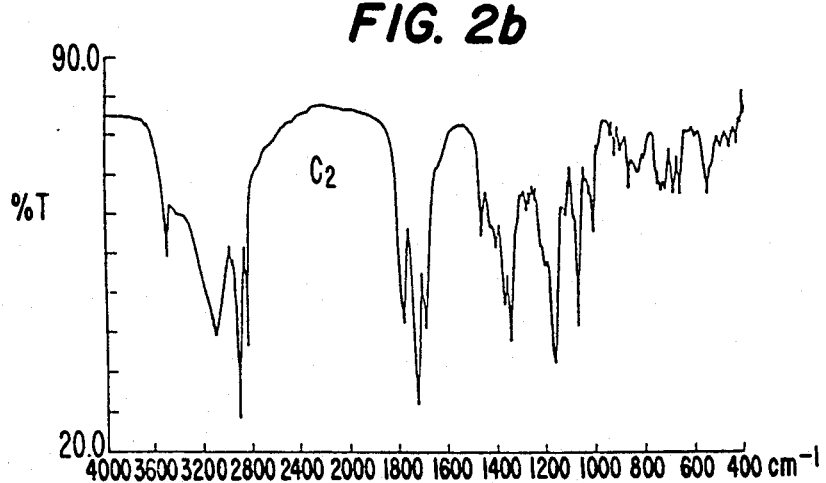
Figure 2C:
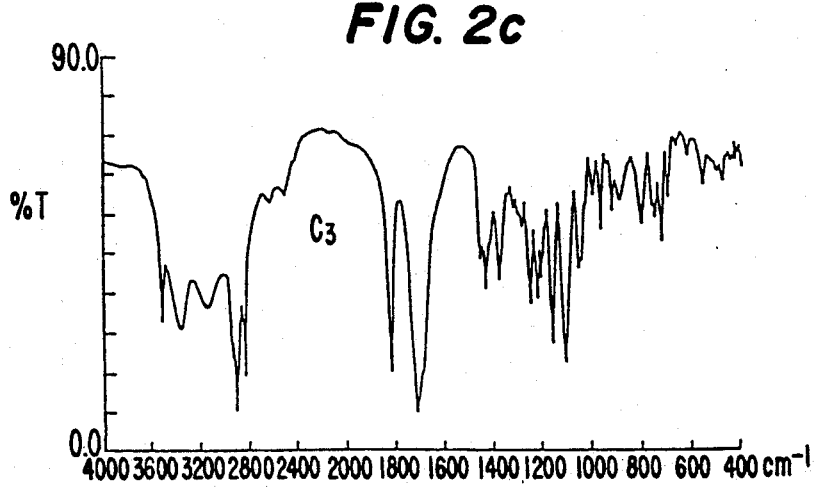

United States Patent [19]

Yoshida et al.

[11] Patent Number: 5,120,647
[45] Date of Patent: Jun. 9, 1992

[54] PHOSPHOLIPASE A$_2$ INHIBITOR

[75] Inventors: Tadashi Yoshida, Osaka; Hiroshi Itazaki, Takarazuka; Hitoshi Arita, Kawanishi; Yoshimi Kawamura, Minoo; Koichi Matsumoto, Toyonaka, all of Japan

[73] Assignee: Shionogi & Co., Ltd., Osaka, Japan

[21] Appl. No.: 617,882

[22] Filed: Nov. 26, 1990

Related U.S. Application Data

[62] Division of Ser. No. 544,673, Jun. 27, 1990.

[30] Foreign Application Priority Data

Jun. 30, 1989 [JP] Japan .................. 1-170396

[51] Int. Cl.$^5$ .............. C12P 17/18; C12P 17/16; C12P 7/42; C12R 1/01
[52] U.S. Cl. .................. 435/119; 435/118; 435/126; 435/135; 435/146; 435/158; 435/252.1
[58] Field of Search ............ 435/118, 119, 126, 135, 435/146, 158, 252.1

[56] References Cited

U.S. PATENT DOCUMENTS 4,145,437  3/1979  Aldridge et al. .................. 424/279

FOREIGN PATENT DOCUMENTS

| 0258814 | 3/1988 | European Pat. Off. |
|---------|--------|---------------------|
| 0359048 | 3/1990 | European Pat. Off. |
| 42-2131 | 1/1967 | Japan. |
| 60-178879 | 9/1985 | Japan. |
| 7309841 | 1/1974 | Netherlands. |

*Primary Examiner*—Herbert J. Lilling
*Attorney, Agent, or Firm*—Wenderoth, Lind & Ponack

[57] ABSTRACT

A compound of the formula (I):

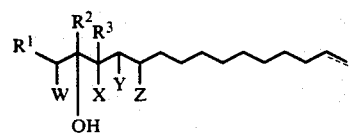

wherein $R^1$, $R^2$, and $R^3$ are —COOR$^4$, —COOR$^5$, and —COOR$^6$, respectively; $R^4$, $R^5$, and $R^6$ each is hydrogen, lower alkyl, or alkali metal; W is hydroxyl; X, Y, and Z each is hydrogen or hydroxyl; a dotted line indicates the presence or absence of a single bond; or where W/R$^3$, X/R$^1$, and/or Z/R$^3$ may be combined together, a lactone is formed, which compound is useful as a phospholipase A$_2$ inhibitor. Process for the production of the compound (I) and a cell culture of a microorganism *Circinotrichum falcatisporum* RF-641 producing the same are also provided.

1 Claim, 4 Drawing Sheets

PHOSPHOLIPASE $A_2$ INHIBITOR

This application is a division of application Ser. No. 07/544,673, filed Jun. 27, 1990.

The present invention relates to a novel phospholipase $A_2$ inhibitor. In particular, it relates to a physiologically active compound capable of inhibiting phospholipase $A_2$, which compound is produced by cultivating *Circinotrichum falcatisporum* RF-641 or a variant thereof capable of producing said compound.

The novel compound of the invention is represented by the formula (I):

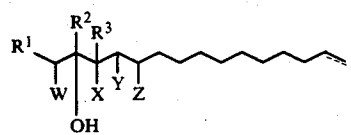

wherein Rhu 1, $R^2$, and $R^3$ are —$COOR^4$, —$COOR^5$, and —$COOR^6$, respectively; $R^4$, $R^5$, and $R^6$ each is hydrogen, lower alkyl, or alkali metal; W is hydroxyl; X, Y, and Z each is hydrogen or hydroxyl; a dotted line indicates the presence or absence of a single bond; or where $W/R^3$, $X/R^1$, and/or $Z/R^3$ may be combined together, a lactone is formed. A compound of formula (I) has been designated as "Cinatrin".

Another aspect of the invention is to provide *Circinotrichum falcatisporum* RF-641 or a variant thereof capable of producing Cinatrin. Further aspect of the invention is a process for the production of Cinatrin which comprises cultivating *Circinotrichum falcatisporum* RF-641 or a variant thereof capable of producing Cinatrin under aerobic fermentation conditions until substantial amount of Cinatrin is produced, isolating resulting products from the culture, and, if desired, hydrolyze and/or esterify said products.

Phospholipase $A_2$, hereinafter referred to as $PLA_2$, which is found in cells or secretory components of various organisms, is an esterase specifically active on phosphorus-containing lipids. More particularly, $PLA_2$ specifically hydrolyzes a fatty acid ester at C-2 position of 1,2-diacylglycerophospholipid to form lysoglycerophospholipid and the fatty acid.

The enzymatic activity of $PLA_2$ often exerts toxic effect on nervous systems, muscles, and heart, and also often causes anticoagulant, which can induce convulsion, arterial hypotension, hemolysis, hemorrhage, and edema. In addition, the esterase is possibly associated with other diseases directly or indirectly. Accordingly, it is generally recognized that a substance inhibiting the enzymatic activity of $PLA_2$ would be useful for the control or treatment of various diseases caused by, or related to, the enzymatic activity of the esterase, as well as for the research of physiological role of $PLA_2$. Those inhibitory substances as mentioned above are herein referred to as $PLA_2$ inhibitors. Examples of known $PLA_2$ inhibitor include Quinacrine (Merck Index) and p-bromophenacyl bromide (Merck Index), and Manoalide (J.B.C. 260 7234 (1985)). However, it has been constantly needed novel $PLA_2$ inhibitors to satisfy the above-mentioned requirements.

The present inventors have made an extensive investigation into many organisms for the production of $PLA_2$ inhibitors and found that some strain of *Circinotrichum*, specifically *Circinotrichum falcatisporum* RF-641 can produce highly selective and potent $PLA_2$ inhibitors. The organism was grown in an appropriate culture, and products having $PLA_2$ inhibitory effect were extracted with organic solvents. The crude product was separated chromatographically into five compounds which differ from one another in physiological and physicochemical properties. Each compound was designated as Cinatrin-A, B, $C_1$, $C_2$ and $C_3$. Structure of each congener was determined using conventional analytical techniques, for example, X-ray analysis, infrared and nuclear magnetic resonance spectroscopy, mass spectrometry, and chemical conversion. They are represented by the following formula (i), (ii), (iii), (iv), and (v), respectively.

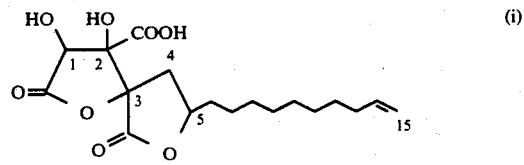

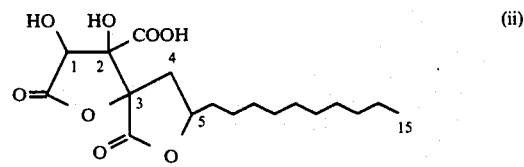

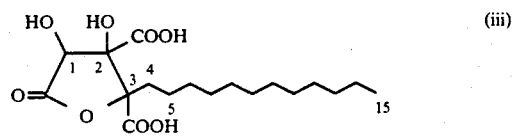

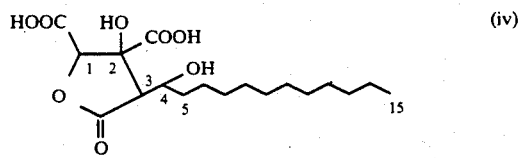

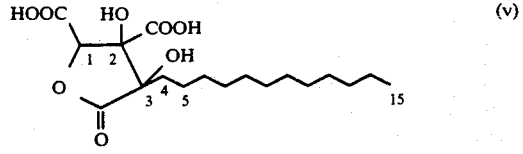

When each of above compounds is subjected to a hydrolytic cleavage in the presence of a base, it gives corresponding seco acid (a hydrolytic ring-opened form) of the formula:

Cinatrin-A seco acid

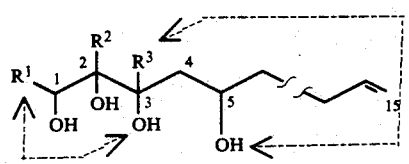

Cinatrin-B seco acid

-continued

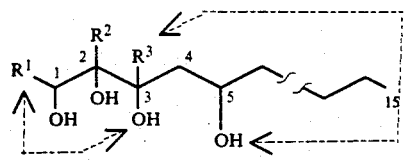

Cinatrin-$C_1$ seco acid

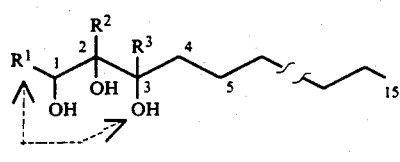

Cinatrin-$C_2$ seco acid

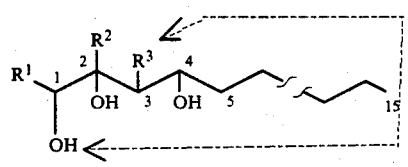

Cinatrin-$C_3$ seco acid

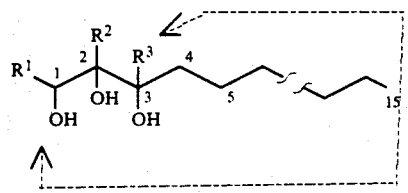

wherein, $R^1$, $R^2$ and $R^3$ are as defined above and the dotted lines indicate the sites of ring-closure.

Cinatrins in a seco acid form as well as those in a lactone form were proved to be effective as $PLA_2$ inhibitors.

It will be easily understood that Cinatrins, in the form of lactone and seco acid, can be converted into esters or salts by well-known procedures in the art. For example, derivatives of Cinatrin A can be prepared according to the process of Reaction Scheme, below.

wherein, $R^1$, $R^2$, $R^3$, and $R^5$ are as defined above, and X is halogen.

Cinatrin B, $C_1$, $C_2$, and $C_3$ can be reacted in the similar manner as above.

These esters and salts as well as lactones and seco acids exert $PLA_2$ inhibiting activity Thus, the present invention provides compounds of the general formula (I) described previously.

The term "lower alkyl" represents a straight or branched alkyl chain bearing one to three carbon atoms, for example, methyl, ethyl, n-propyl, and isopropyl.

The term "alkali metal" represents sodium, potassium, and lithium.

While all the compounds of the present invention are believed to inhibit $PLA_2$, certain of those are especially preferred for such use. Preferred Cinatrins are those wherein $R^1$, $R^2$, and $R^3$ are —$COOR^4$, —$COOR^5$ and —$COOR^6$, respectively, $R^4$, $R^5$ and $R^6$ are each selected from the group consisting of hydrogen, lower alkyl, or alkaline metal.

Hydrolysis and Esterification of Cinatrin A—$C_3$ can be carried out according to any of known processes in the art, as exemplified below.

Hydrolysis: Cinatrins A—$C_3$ (lactone) can be each hydrolyzed in an aqueous solution of a strong base such as a hydroxide of an alkali metal, for example, sodium hydroxide, potassium hydroxide, or lithium hydroxide. The reaction is conducted for about 5 minutes to about 12 hours at a temperature in the range of from room temperature to about 100° C., preferably, for about 5 minutes to about 10 hours at 100° to 60° C. or about 1 to about 12 hours at room temperature, while stirring. Under these conditions, hydrolysis and ring-opening are completed and the starting compound is converted into corresponding seco-Cinatrin (tricarboxylic acid).

Alternatively, an ester having lactone ring can be subjected to ring-opening and resultant ester containing one or two carboxyl groups is then converted into tri-ester using an alkyl halide. The obtained tri-ester can be hydrolyzed to give tri-carboxylic acid.

Esterification: A selected Cinatrin having lactone ring is reacted with an alkanol having 1 to 3 carbon atoms in an appropriate organic solvent in the presence of an organic or inorganic acid for about 30 minutes to about 5 hours at a temperature in the range of from room temperature to about 200° C. Examples of appro-

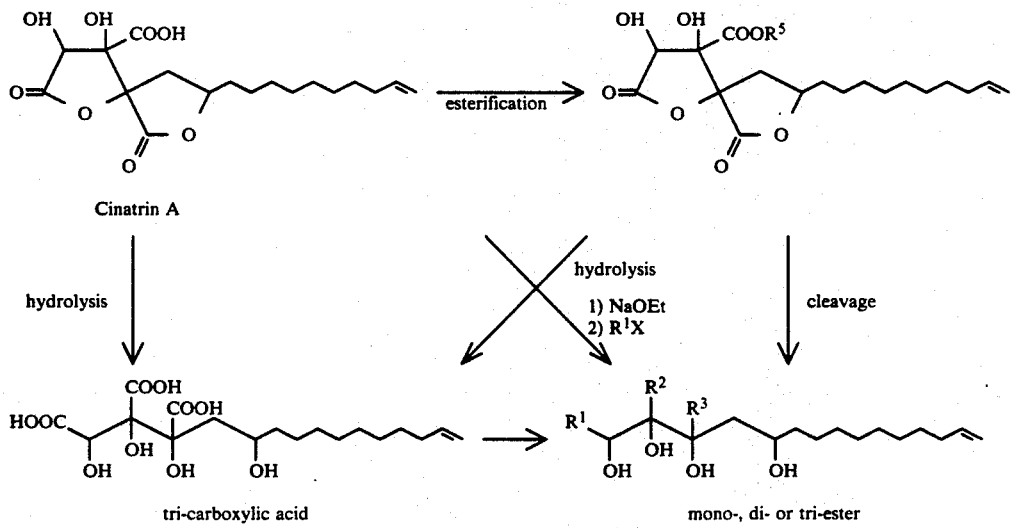

priate organic or inorganic acid include hydrochloric acid, sulfuric acid, toluenesulfonic acid, trifluoromethanesulfonic acid, methanesulfonic acid, trifluoroborate, and acetic anhydride. Acidic ion-exchanging resins or enzymes are also available as catalysts. Alternatively, the esterification can be carried out at room temperature using a diazoalkane, such as diazomethane.

Solvents which may be used in the esterification include methanol, ethanol, propanol, and tetrahydrofuran.

When a Cinatrin having lactone ring is reacted with an alcoholate and corresponding alkanol, the ring-opening and esterification can be effected simultaneously, which result in an ester of seco acid.

The present invention further provides a biologically pure culture of Circinotrichum falcatisporum RF-641 which produces $PLA_2$ inhibitor, Cinatrin. The culture of the Cinatrin-producing strain was deposited with the Fermentation Research Institute, Agency of Industrial Science and Technology, 1-3, Higashi 1 chome, Tsukuba-shi, Ibaraki-ken, Japan, under accession number of FERM P-10681 on Apr. 21, 1989, and then the deposition was converted to the deposition under Budapest Treaty on Feb. 6, 1990, and assigned accession No. FERM BP-2752.

Cultural characteristics of *Circinotrichum falcatisporum* RF-641 are described below.

The strain does not exhibit typical morphological properties on the agar media. The morphological properties on a leaves are described below.

Colonies are punctiform to effused, dark brown to black, hairy, and composed of dark, branched and anastomosing hyphae bearing setae and sporogenous cells. Setae arising from dark brown, thick-walled and swollen cells of the superficial mycelium, are numerous, simple, erect, thick-walled, sparsely, and indistinctly septate, roughened, dark brown, opaque, darker near the base, paler towards the apex which is circinate or spirally twisted. Sporogenous cells are numerous, arising laterally on the superficial hyphae, obclavate to lageniform, thin-walled, subhyaline. Conidia are adherent, persisting at the bases of setae in the form of a whitish pellicle, falcate with acute ends, 18.5–20.0×1.7 μm.

Based on the taxonomic properties described above, the strain RF-641 is identified as *Circinotrichum falcatisporum* Pirozynski (1962) which is described in Mycological Papers 84, 7–8, 1962.

As is the case with other organisms, the culture of the Cinatrin-producing culture of the present invention, *Circinotrichum falcatisporum* RF-641 may be subject to variation. Mutation of the strain may naturally occur, but may be easily induced by treatment with various physical and chemical mutagens. Accordingly, those skilled in the art will understand that variants of *Circinotrichum falcatisporum* RF-641 fall within the scope of the invention insofar as they maintain their abilities producing a substantial amounts of $PLA_2$ inhibitor.

Cultivation of *Circinotrichum falcatisporum* RF-641 may be conducted by conventional aerobic fermentation methods.

Culture media and conditions are selected from those generally employed in the field of producing antibiotics.

The medium contains carbon sources, nitrogen sources, mineral salts, and the like. Vitamins and precursors may be added to it, if necessary. Carbon sources which are preferred in a culture medium include, for example, glucose, starch, dextrin, glycerin, molasses, organic acids and a mixture thereof. Nitrogen sources which are preferred in a culture medium include, for example, soy flour, corn-steap-liquor, meat extract, yeast extract, cotton sead flour, peptone, wheat germ, ammonium sulfate, ammonium nitrate, and a mixture thereof. Examples of mineral salts include calcium carbonate, sulfate of magnesium, copper or zinc, chloride of sodium, potassium, manganese or cobalt, and various phosphates. These mineral salts can be added to the medium in case of need.

When *Circinotrichum falcatisporum* RF-641 is grown under aerobic culture conditions in a selected medium at temperature ranging from about 25°–30° C., a substantial amounts of Cinatrin is accumulated in the culture. The produced Cinatrin is then recovered from the culture by methods generally used in the art of fermentation. Cinatrin ca be efficiently separated by extracting fermentation broth with an appropriate organic solvent under acidic conditions. The extract is then concentrated. The crude extract containing a mixture of Cinatrins is then purified and separated into Cinatrin A, B, $C_1$, $C_2$, and $C_3$ chromatographically.

Purified Cinatrins so obtained may be converted into seco acids, esters, and the like, optionally.

Organic solvents which can be used for the extraction include ethyl acetate, n-butanol, methyl ethyl ketone, and the like. Preferred solvent is ethyl acetate. Extraction is conducted under acidic conditions, generally from about pH 1–5, preferably pH 2.

The structure of each compound was determined by X-ray analysis, chemical conversion, and IR, NMR and MS spectrometry.

Cinatrins (lactone, ester and seco acid) of the invention inhibited the activity of $PLA_2$ derived from rat platelet. The amount of Cinatrin (μg/ml) effective for inhibiting 50% of $PLA_2$ activity ($IC_{50}$) was determined. The results are shown in Table 1.

TABLE 1

Inhibitory Effect of Various Cinatrin Derivative on $PLA_2$ from Rat Platelet $IC_{50}$ (μg/ml)

| | Cinatrins | | |
|---|---|---|---|
| | lactone form | methyl ester | seco acid (Na salt) |
| Cinatrin A | 117 | 83.2 | 56.2 |
| Cinatrin B | 54.9 | 83.2 | 30.9 |
| Cinatrin $C_1$ | >300 | 57.2 | 27.5 |
| Cinatrin $C_2$ | 300 | 300 | 17.5 |
| Cinatrin $C_3$ | 29.5 | 53.7 | 27.5 |

The above Table 1 shows that Cinatrin B and $C_3$ are particularly effective. Furthermore, although $C_1$ is moderately active in its lactone form, it becomes more active when it is converted into an ester or seco acid form.

Cinatrins of the invention is considered to be clinically useful in the therapeutic and prophylactic treatments of various diseases caused by enzymatic activity of $PLA_2$, as research of physiological activities of $PLA_2$.

BRIEF DESCRIPTION OF DRAWINGS

In the accompanying drawings, FIG. 1 shows IR spectra of Cinatrin A and $C_1$, FIG. 2 shows IR spectra of Cinatrin B, $C_2$ and $C_3$. FIG. 3 shows IR spectra of Cinatrin A and B seco acids Na. FIG. 4 shows IR spectra of Cinatrin $C_1$, and $C_3$ seco acids Na.

Following Examples further illustrate the present invention. The Examples are not intended to be limiting the scope of the invention in any respect and should not be so construed.

EXAMPLE 1

Preparation of Cinatrin

1) Fermentation of *Circinotrichum falcatisporum* RF-641

Potato-glucose agar slant was prepared by pouring 10 ml of potato-glucose agar into test tubes of middle size and sterilizing the same. Each tube was inoculated with *Circinotrichum falcatisporum* RF-641 and incubated at 25°-28° C. for 10-14 days. One to two loopfuls of culture from the agar slant was inoculated into 100 ml culture medium (1.0% polypeptone, 2.0% glucose, 0.3% meat extract, 0.2% yeast extract, 0.1% sodium chloride, and tap water, (pH=7.0, pre-sterilization)) in a 500 ml Sakaguchi flask. The flask was then incubated at 28° C. with a 120 rpm shaking rate for 72 hours. A portion (3.2 ml each) of the shaken culture was inoculated into 500 ml volume Erlenmyer flasks ($\times$130) each containing 80 ml culture medium (prepared by mixing 1000 ml of potato decoction, and 20 g sucrose). Each flask was incubated at 28° C. with a 180 rpm shaking rate for 96 hours.

The potato decoction was prepared by cutting potatoes (200 g) into about 1 cm cubes, boiling the cubes in water (1000 ml) at 105° C. for 15 minutes, and filtering the mixture through gauze.

2) Isolation

A. Crude Extraction

Ten L of fermentation broth (pH 7.0-6.8) obtained in the same manner as above was adjusted to pH 2.0 with 1N HCl and extracted using 3 L of ethyl acetate. The extract was washed with about 30% NaCl, dried over sodium sulfate, and concentrated under reduced pressure. The concentrate was then dissolved in 500 ml of hexane and hexane-soluble substances were removed to obtain 14.5 g of hexane-insoluble crude extract.

B. Isolation of Cinatrin

To a solution of 14.5 g of the above crude extract in 40 ml of methanol was added 60 ml of 0.1% trifluoroacetic acid (total volume of 100 ml). The solution was then applied to a CHP-20P column (Mitsubishi Chemicals, Tokyo, Japan, 75-150 μm, 400 ml volume). The column was eluted with a linear gradient starting from 40% methanol in 0.1% trifluoroacetic acid to 90% methanol in 0.1% trifluoroacetic acid, collecting 15 g fractions, run at a flow rate of 15 ml/min. Eluate was monitored by UV at 210 nm. Fractions containing Cinatrin A and B (Pools A and B) and those containing Cinatrin $C_1$, $C_2$, and $C_3$ (Pool C) were separately collected by monitoring each fraction with thin layer chromatography (TLC) and analytical high performance liquid chromatography (analytical HPLC) as shown below.

TLC

Plate: Merck Pre-Coated TLC Plates SILICA GEL 60 F-254

Solvent: chloroform/methanol/$H_2O$ (2/2/1) (lower layer): acetic acid = 9:1

Detection: UV at 254 nm, and phosphomolybdic acid ($P_2O_5 \cdot 24MoO_3 \cdot nH_2O$)

Rf: Cinatrin A=B=0.47, $C_1=C_2=C_3=0.29$

Analytical HPLC

Column COSMOSIL $5C_{18}$ (4.6$\times$250 mm)

Detection: UV at 210 nm

Flow rate: 1 ml/min

Solvent: acetonitrile aq./0.1% TFA (55:45)

Retention time (min): Cinatrin A=12.7, B=20.2, $C_1=12.4$, $C_2=13.1$, $C_3=14.8$ Above systems were also employed in the following procedures.

C. Isolation and Purification of Cinatrin (1) Isolation of Cinatrin A (C A name: 1,2,3,5-tetrahydroxy-14-pentadecene-1,2,3-tricarboxylic acid, (1→3)-τ-lactone, (3→5)-τ-lactone; General name: 8-(dec-9-ene-1-yl)-3,4-dihydroxy-2,6-dioxo-1,7-dioxaspiro[5,5]-nonane-4-carboxylic acid)

The Pools A and B prepared as described in above B were concentrated under reduced pressure to yield 1.07 g of a mixture of Cinatrin A and B. The concentrate was applied to a column chromatography using a mixture of acetonitrile and 0.1% trifuluoroacetic acid (55:45) as an eluting agent.

Column chromatography

Column: Lichroprep RP-18 (Merck), 25-40 μm (20$\phi \times$500 mm)

Flow rate: 5 ml/min

Detection: UV at 210 nm

Collection: 15 g fraction

The eluate was monitored by TLC and analytical HPLC as described above. Fractions containing Cinatrin A and those containing B were pooled separately. The former was concentrated under reduced pressure to give 320 mg of crude Cinatrin A. It was then purified by preparative HPLC using acetonitrile and 0.1% trifluoroacetic acid (55:45) as an eluting solvent.

Preparative HPLC

Column: COSMOSIL $5C_{18}$ (20$\phi \times$150 mm), (Nakarai Chemicals, Inc.)

Detection: UV at 210 nm

Flow rate: 8 ml/min

Retention time: 20 min (Cinatrin A)

Fractions containing Cinatrin A were collected and evaporated in vacuo to yield 140 mg of an acidic, amorphous and colorless powder. The physicochemical properties of purified Cinatrin A are listed below.

1. Solubility: soluble in water and organic solvents
2. Molecular formula: $C_{18}H_{26}O_8$ (mw 370) SIMS: m/z 371 $[M+Z]^+$, calculated for $C_{18}H_{26}O_8+H$
3. $[\alpha]_D^{25.5}$: $-20.1\pm2.0°$ (c 0.303, MeOH)
4. UV spectrum: UV$\lambda_{max}^{MeOH}(E_{1\,cm}^{1\%})$: 220 nm (11)
5. IR spectrum: IR$\nu_{max}^{KBr}$cm$^{-1}$: 3420, 2928, 2856, 1776, 1747, 1641, 1468, 1446, 1349, 1226, 1151, 1063, 992, 908, 840, 780, 720
6. NMR spectrum: $^1$H-NMR (200 MHz) ($d_6$-DMSO) ppm: (internal standard TMS): 1.27(12H,m), 1.64(2H,m), 2.03(2H,m), 2.37(2H,m), 4.54(1H,m), 4.74(1H,s), 4.90-5.04(2H,m), 5.69-5.90(1H,m), 6.7(1H,br,OH), total 24H $^{13}$C-NMR (50 MHz) ($d_6$-DMSO) ppm: (internal standard TMS): 18 carbon signals; 9 methylenes {24.4(t), 28.2(t), 28.5(t), 28.6(t), 28.7(t), 28.8(t), 33.2(t), 34.4(t), 36.2(t)}, 2 methines {72.8(d), 77.3(d)}, 2 quaternary carbons {83.8(s), 84.3(s)}, olefinic carbons {114.9(t), 139.1(d)}, carbonyl carbons {169.9(s), 172.7(s), 172.8(s)}

7. Structural Analysis: The structure was determined on the basis of data of SIMS and NMR. The spectra in $^1$H NMR and $^{13}$C NMR are similar to that of Ciantrin B (below) showing 9 methylene $CH_2$ except for that they indicate the existence of a terminal double bond ($-^{13}CH_2-^{14}CH=^{15}CH_2$) instead of terminal ($^{15}CH_3{}^{14}CH_2-$). On catalytic reduction ($H_2$ on 5% Pd-C in methanol), it was converted into Cinatrin B. These results suggest that it has a spiro-dilactone ring analogous to Cinatrin B and a side chain with a terminal bond of $^{14}CH=^{15}CH_2$.

(2) Isolation of Cinatrin B (C A name: 1,2,3,5-tetrahydroxy-pentadecane-1,2,3-tricarboxylic acid, (1→3)-τ-lactone; General name: 8-(decane-1-yl)-3,4-dihydroxy-2,6-dioxo-1,7-dioxaspiro[5,5]-nonane-4-carboxylic acid)

The remainder of fractions obtained in above (1) was concentrated under reduced pressure and the residue (440 mg) was chromatographed by Lichroprep RP-18 column in the same manner as above (1). The column was developed with a mixture of trifluoroacetic acid and methanol (30:70). The eluate was concentrated under reduced pressure and lyophilized to give 270 mg of purified Cinatrin B as an acidic, amorphous and colorless powder. The physicochemical properties of purified Cinatrin B are listed below.

1. Solubility: soluble in organic solvents
2. Molecular formula: $C_{18}H_{28}O_8$ (mw 372) SIMS: m/z 373 $[M+H]^+$, calculated for $C_{18}H_{28}O_8+H$ Anal. Calcd. (%) for $C_{18}H_{28}O_8 \cdot \frac{1}{2}H_2O$: C, 56.68; H, 7.66. Found (%): C, 56.68; H, 7.53.
3. $[\alpha]_D^{24}$: $-24.4\pm2.1°$ (c=0.308 MeOH)
4. UV spectrum: UV $\lambda_{max}^{MeOH}$: 220 nm ($E_1$ $cm^{1\%}$=12)
5. IR spectrum: IR $\nu_{max}^{KBr}$:3394, 2918, 2850, 1795, 1767, 1750(sh), 1470, 1362, 1229, 1195, 1150, 1084, 1052, 993, 973, 837, 811, 780, 719, 447

IR $\nu_{max}^{CHCl_3}(cm^{-1})$: Free: 3600-2200, 2924, 2852, 1805(sh), 1784, 1737, 1464, 1357, 1150, 1071, 1038, 1011, 870, 838

6. NMR spectrum: $^1$H-NMR (200 MHz) ($d_6$-DMSO) ppm: (internal standard TMS): 0.86(3H,t), 1.25(16H,s like), 1.63(2H,m), ca 2.38(2H,dd×2), 4.52(1H,m), 4.73(1H,s) $^{13}$C-NMR (100 MHz) ($d_6$-DMSO) ppm: (internal standard TMS): 13.85(q), 21.98(t), 24.36(t), 28.52-28.84(t×4-5), 31.18(t), 34.30(t), 36.17(t), 72.60(d), 77.06(d), 83.57(s), 84.05(s), 169.46(s,C=O), 172.28(s,C=O), 172.37(s,C=O)

7. Color reaction negative—Ehrlich, 2,4-Dinitorophenylhydrazine, Dragendolff, Ninhydrin; positive—Bromocrezolegreen (BCG), $I_2$, $H_2SO_4$-heat, phosphomolybdic acid 8. Structural Analysis: NMR and IR data indicate that the molecule contains three $-C=O$ groups. As one of them is attributed to $-COOH$, the remainders are assumed to di-lactone or anhydrides.

(3) Isolation of Cinatrin $C_1$ (C A name: 1,2,3,5-trihydroxy-pentadecane-1,2,3-tricarboxylic acid, (1→3)-τ-lactone; General name: 2-dodecyl-3,4-dihydroxy-5-oxo-tetrahydrofuran-2,3-dicarboxylic acid)

The Pool C prepared as described in above B was concentrated under reduced pressure to yield 2.85 g of a mixture of Cinatrin $C_1$, $C_2$ and $C_3$. The concentrate was applied to a Lichroprep RP-18 column and chromatographed in the same manner as above (1) using a mixture of 0.1% trifluoroacetic acid and methanol (50:50) as an eluent. Eluate was monitored by TLC and analytical HPLC and fractions containing Cinatrin $C_1$, $C_2$ or $C_3$ were pooled separately.

Eluate containing Cinatrin $C_1$ was concentrated under reduced pressure and the residue (600 mg) was chromatographed again using Lichroprep RP-18 column (Merck, 25-40 μm (20ϕ×500 mm)) in the same manner as above (1) using a mixture of 0.1% trifluoroacetic acid and acetonitrile (50:50) as an eluent. Fractions containing Cinatrin $C_1$ were evaporated under reduced pressure to yield 260 mg of residue, which was then purified by preparative HPLC using COSMOSIL 5$C_{18}$ in the same manner as above (1) except for that the retention time is 28 minutes. Fractions containing Cinatrin $C_1$ were combined, concentrated and lyophilized to give 159 mg of purified Cinatrin $C_1$ as an acidic, amorphous and colorless powder. The physicochemical properties of purified Cinatrin $C_1$ are listed below.

1. Solubility: soluble in organic solvents, slightly soluble in water
2. Molecular formula: $C_{18}H_{30}O_8$ (mw 374): SIMS m/z 375 $[M+H]^+$, calculated for $C_{18}H_{30}O_8+H$
3. $[\alpha]_D^{24}$: $-11.2\pm1.6°$ (c=0.314, MeOH)
4. UV spectrum: UV $\lambda_{max}^{MeOH}(E_1 {}_{cm}{}^{1\%})$: 220 nm (11)
5. IR spectrum: IR $\nu_{max}^{KBr}$: 3536, 3460, 3288, 2920, 2852, 1785, 1739, 1661, 1467, 1434, 1403, 1378, 1243, 1225, 1186, 1169, 1123, 1037, 1016, 984, 920, 879, 822, 777, 759, 719, 668, 638, 602, 500
6. NMR spectrum: $^1$H-NMR (200 MHz) ($d_6$DMSO)ppm: 0.84(3H,t), 1.22(16-H,m), 1.55(1H,m), 2.04(1H,m), 4.54(1H,s), 6.34(1H,b,OH)

$^{13}$C-NMR (50 MHz) ($d_6$-DMSO) ppm: 18 carbon signals; methyl carbon {13.9(q)}, 11 methylenes {22.1(t), 23.5(t), 28.7-29.3(t×7), 30.8(t), 3 3(t)}, methine {73.1(d)}, 2 quaternary carbon {84.0(s), 86.6(s)}, 3 carbonyl carbons {170.4(s), 170.6(s), 173.6(s)}

7. Structural Analysis a) As the compound forms dimethyl ester in the reaction with diazomethane, it contains two carboxyl groups.

b) Molecular formula obtained from SIMS agrees with that calculated for $C_{18}H_{30}O_8$.

c) In $^{13}$C NMR spectrum, 18 signals are observed. The spectrum is similar to that of Cinatrin $C_3$ (below), i.e., one methyl ($CH_3$), 11 methylenes ($CH_2$), 1 methine (CH), 2 quaternary carbon atoms, and 3 carbonyl carbon atoms (C=O) consisting of 2 carboxylic acids.

d) When the compound was kept in 0.05N NaOH for 2 hours at the room temperature, it was cleaved to give seco acid. The reaction mixture was then adjusted to pH 1 with 1N HCl and allowed to stand for overnight to obtain a mixture of Cinatrin $C_3$ and Cinatrin $C_1$ (1:1, by HPLC). These results suggest that the compound is produced by re-lactonization of Cinatrin $C_3$. Therefore it was concluded to be a (1→3)-τ-lactone which has $-OH$ and $-COOH$ groups in the different positions from Cinatrin $C_3$.

(4) Isolation of Cinatrin $C_2$: (1,2,4-trihydroxy-pentadecane-1,2,3-tricarboxylic acid, (3→1)-τ-lactone; or 3-hydroxy-4-(1-hydroxydodecyl)-5-oxo-tetrahydrofuran-2,3-dicarboxylic acid)

Fractions containing Cinatrin $C_2$ prepared as described above (3) was combined and concentrated under reduced pressure. The residue (330 mg) was applied to a preparative HPLC using COSMOSIL 5$C_{18}$ in the same manner as above (3) except for that the retention time is 33 minutes (Cinatrin $C_2$). Fractions containing Cinatrin $C_2$ were combined and evaporated under reduced pressure to yield 100 mg of crude product, which was then purified by the recrystallization from methanol/water to obtain 73 mg of purified Cinatrin $C_2$ as an acidic, colorless and fine needles. m.p. 152°–154° C. The physicochemical properties of purified Cinatrin C$_2$ are listed below.

1. Solubility: soluble in organic solvents
2. Molecular formula: C$_{18}$H$_{30}$O$_8$ (mw 374) SIMS: m/z 375 [M+H]$^+$, calculated for C$_{18}$H$_{30}$O$_8$+H Anal. Calcd. (%) for C$_{18}$H$_{30}$O$_8$·½H$_2$O: C, 57.05; H, 8.11. Found (%): C, 57.23; H, 8.07.
3. [α]$_D^{24}$: −54.5±3.0° (c=0.312, MeOH)
4. UV spectrum: UV λ$_{max}^{MeOH}$: end absorption
5. IR spectrum: IR ν$_{max}$cm$^{-1}$: Free (KBr); 3504, 3420, 3120, 2916, 2846, 1779, 1725, 1688, 1467, 1407, 1371, 1347, 1166, 1077, 1016, 867, 754–660(5 bands), 551
6. NMR spectrum: $^1$H-NMR (200 MHz) (d$_6$-DMSO) ppm: (internal standard TMS): 0.86(3H,t), 1.24(about 20H,s like), 1.53(2H,m), 3.15(1H,d), 3.81(1H,s like), 5.12(1H,s)

$^{13}$C-NMR (50 MHz) (d$_6$-DMSO) ppm: (internal standard TMS): 13.92(q), 22.06(t), 25.06(t), 28.70–29.03(t-×3–6), 31.28(t), 33.34(t), 53.69(d), 66.99(d), 80.60(s), 81.21(d), 166.86(s,C=O), 172.10(s,C=O), 173.61(s,C=O)

From the above data, the compound is assumed to have a 5-membered lactone ring.

7. Color reaction: negative—Ehrlich, 2,4-Dinitorophenylhydrazine, Dragendolff, Ninhydrin; positive—Bromocrezolegreen (BCG), I$_2$, H$_2$SO$_4$-heat, phosphomolybdic acid (5) Isolation of Cinatrin C$_3$: (1,2,3-trihydroxy-pentadecane-1,2,3-tricarboxylic acid, (3→1)-τ-lactone; or 4-dodecyl-3,4-dihydroxy-5-oxo-tetrahydrofuran-2,3-dicarboxylic acid)

Fractions containing Cinatrin C$_3$ prepared as described above (3) were concentrated under reduced pressure. The residue (550 mg) was recrystallized from methanol/water to obtain 463 mg of purified Cinatrin C$_3$ as an acidic, colorless and fine needles. m.p. 205°–207° C. (in THF-n-hexane). The physicochemical properties of purified Cinatrin C$_3$ are listed below.

1. Solubility: soluble in organic solvents
2. Molecular formula: C$_{18}$H$_{30}$O$_8$ (mw 374)

SIMS: m/z 467 [M+Gly]$^+$, calculated for C$_{18}$H$_{30}$O$_8$+Gly

Anal. Calcd. (%) for C$_{18}$H$_{30}$O$_8$: C, 57.74; H, 8.08. Found (%): C, 57.51; H, 8.00.
3. [α]$_D^{24}$: −86.1±2.4° (c=0.519%, MeOH)
4. UV spectrum: UV λ$_{max}^{MeOH}$: 220 nm (sh) E$_1$ cm$^{1\%}$=10
5. IR spectrum: IR ν$_{max}^{KBr}$cm$^{-1}$: 3526, 3376, 3154, 2952, 2910, 2846, 1824, 1723, 1695, 1463, 1438, 1380, 1254, 1226, 1163, 1115, 1059, 967, 920, 806, 723 (5-membered lactone)
6. NMR spectrum: $^1$H-NMR (200 MHz) (d$_6$-DMSO) ppm: (internal standard TMS): 0.86(3H,t), 1.24(about 18H,s like), 1.43(2H,m), 1.70(2H,m), 5.32(1H,s)

$^{13}$C-NMR (50 MHz) (d$_6$-DMSO) ppm: (internal standard TMS): 13.95(q), 21.10(t), 22.11(t), 28.76(t), 29.07–29.12(t×5), 29.70(t), 30.59(t), 31.34(t), 78.92(s), 79.68(d), 81.51(s), 167.93(s), 170.90(s), 175.05(s)

The structure was confirmed to be a carboxylic acid having a 5-membered lactone ring by means of X-ray analysis. The confirmed structure is consistent with the structure assumed from IR and NMR data.

7. Color reaction: negative—Ehrlich 2,4-Dinitorophenylhydrazine, Dragendolff, Ninhydrin; positive—Bromocrezolegreen (BCG), I$_2$, H$_2$SO$_4$-heat, phosphomolybdic acid

EXAMPLE 2

Preparation of Cinatrin Methyl Ester

To a solution of Cinatrin A (50 mg, prepared as described in Example 1) in a mixture of 5 ml of tetrahydrofuran and 10 ml of diethylether, is added excess of ethereal solution of diazomethane while cooling on ice. After standing for 30 min at room temperature, three drops of glacial acetic acid is added to it. The mixture was concentrated to dryness to yield crude product, which was then purified by TLC (plate: Merck Pre-Coated TLC Plates SILICA GEL F-254, 0.5 mm; solvent: dichloromethane/methanol (95:5); Rf=0.32). The eluate was concentrated in vacuo and the concentrate (48 mg) was purified by preparative HPLC. Eluate was concentrated under reduced pressure to give 28 mg (yield 54%) of purified methyl ester of Cinatrin A.

Preparative HPLC

Column: COSMOSIL 5C$_{18}$ (20ϕ×150 mm) (Nakarai Chemicals),
Solvent: 80% aqueous acetonitrile,
Flow rate: 1.0 ml/min,
Retention time: 5.3 min Methyl esters of Cinatrins B, C$_1$, C$_2$, and C$_3$ were prepared in the same manner as above. The amount of starting material and yield of each reaction are listed in Table 2.

TABLE 2

| Cinatrin | Amount (mg) | Methyl ester (mg) | yield (%) |
| --- | --- | --- | --- |
| B | 70 | 34 | 47 |
| C$_1$ | 48 | 33 | 63 |
| C$_2$ | 6.5 | 2.4 | 34 |
| C$_3$ | 20 | 14 | 64 |

Rf values in TLC and retention times (Rts) in preparative HPLC for each ester are as follows:

| | Cinatrin methyl ester | | | |
| --- | --- | --- | --- | --- |
| | B | C$_1$ | C$_2$ | C$_3$ |
| Rf | 0.51 | 0.32 | 0.40 | 0.34 |
| Rt | 7.2 | 9.1 | 9.9 | |

The physicochemical properties of methyl ester of each Cinatrin are listed below.

Cinatrin A methyl ester

1. SIMS: m/z 385 [M+H]$^+$, calculated for C$_{19}$H$_{28}$O$_8$+H
2. NMR spectrum:

$^1$H-NMR (200 MHz) (CDCl$_3$) ppm (internal standard TMS) 1.29(12H,m), 1.56–1.88(2H,m), 2.04(2H,m), 2.32(2H,m), 3.95(3H,s), 4.32(1H,s,OH), 4.47(1H,m), 4.89–5.06(2H,m), 5.26(1H,s), 5.71–5.92(1H,m), total 27×H $^{13}$C-NMR (50 MHz) (CDCl$_3$) ppm: (internal standard TMS): 19 carbon signals, 9 methylenes {25.1(t), 29.1(t), 29.3(t), 29.4(t), 29.5(2×t), 34.0(t), 35.7(t), 36.7(t), 54.7(q, OCH$_3$)}, 2 methines {73.4(d), 78.1(d)}, 2 quaternary carbons {83.9(s), 84.7(s)}, olefinic carbons {114.6(t), 139.7(d)}, 3 carbonyl carbons {170.2(s , 171.7(s), 172.1(s)}

Cinatrin B methyl ester

1. SIMS: m/z 387 [M+H]$^+$, calculated for $C_{19}H_{30}O_8$+H
2. IR spectrum: IR$\nu$max CHCl$_3$ cm$^{-1}$: 3550, 3502, 3022, 2924, 2852, 1814, 1785, 1746, 1462, 1439, 1370, 1279, 1150, 1118, 1069, 1014, 959, 834
3. NMR spectrum: $^1$H-NMR (200 MHz) (d$_6$-DMSO) ppm: (internal standard TMS): 0.86(3H,t), 1.23(16H,s like), 1.63(2H,m), ca 2.36(2H,dd×2), 3.76(3H,s,OCH$_3$), 4.53(1H,m), 4.76(1H,d), 6.85(1H,d,OH), 7.39(1H,s,OH)

$^{13}$C-NMR (50 MHz) (d$_6$-DMSO) ppm: (internal standard TMS): Me ester (50 MHZ); 13.89(q), 22.05(t), 24.38(t), 28.60(t), 28.67(t), 28.81(t), 28.91(t), 28.95(t), 31.27(t), 34.39(t), 36.01(t), 52.98(q), 73.16(d), 77.39(d), 88.44(s×2), 169.13(s,C=0), 172.43(s,C=0), 172.55(s,C=0)

Cinatrin C$_1$ dimethyl ester

1. SIMS: m/z 403 [M+H]$^+$, calculated for $C_{20}H_{34}O_8$+H
2. NMR spectrum: $^1$H-NMR (200 MHz) (CDCl$_3$) ppm: 0.85(3H,t), 1.22(16-H,m), 1.30-1.70(1H,m), 2.08(1H,t) 3.81(3H,s,OCH$_3$), 3.89(3H,s,OCH$_3$), 4.05(1H,b,OH), 4.88(1H,s), total 29-H $^{13}$C-NMR (50 MHz) (CDCl$_3$) ppm: 20 carbon signals; methyl {14.3(q), 11 methylenes {22.9(t), 24.1(t), 29.4(t), 29.5(t), 29.6(t), 29.7(t), 29.9(t×3), 31.7(t), 32.1(t)}, 53.6(q,OCH$_3$), 54.2(q,OCH$_3$), methine {73.4(d)}, 2 quaternary carbons {84.8(s), 87.3(s)}, 3 carbonyl carbons {169.0(s), 170.2(s), 173.0(s)}

Cinatrin C$_2$ dimethyl ester

1. SIMS: m/z 403 [M+H]$^+$, calculated for $C_{20}H_{34}O_8$+H
2. IR spectrum: IR$\nu$max (CHCl$_3$) cm$^{-1}$: 3355, 3505, 2957, 2927, 2855, 1781, 1751, 1602, 1457, 1441, 1352, 1317, 1273, 1171, 1145, 1098, 1038, 509 (5-membered lactone)
3. NMR spectrum: $^1$-NMR (200 MHz) (d$_6$-DMSO) ppm: (internal standard TMS): 0.82(3H,t), 1.23(ca 20H,s like), 1.45(2H,m), 3.21(1H,d), 3.66(3H,s,OCH$_3$), 3.76(3H,s,OCH$_3$), 3.82(1H,q), 4.96(1H,d,OH), 5.25(1H,s), 6.66(1H,s,OH)

$^{13}$C-NMR (50 MHz) (d$_6$-DMSO) ppm: (internal standard TMS): 13.95(q), 22.11(t), 25.04(t), 28.74(t), 28.89(t), 28.70-29.04(t×4), 31.34(t), 33.29(t), 52.40(q), 53.15(q), 53.75(d), 66.86(d), 81.07(s), 81.14(d), 165.88(s), 170.86(s), 172.88(s)

Cinatrin C$_3$ dimethyl ester

1. SIMS: m/z 403 [M+H]$^+$, calculated for $C_{20}H_{34}O_8$+H
2. IR spectrum: IR $\nu$max (CHCl$_3$) cm$^{-1}$: 3373, 3506, 2958, 2927, 2855, 1801, 1754, 1602, 1457, 1440, 1362, 1275, 1175, 1129, 1102, 507, 494 (lactone)
3. NMR spectrum: $^1$-NMR (200 MHz) (d$_6$-DMSO) ppm: (internal standard TMS): 0.86(3H,t), 1.23(ca 18H,s like), 1.40(2H,m), 1.70(2H,m), 3.67(3H,s,OCH$_3$), 3.73(3H,s,OCH$_3$), 5.51(1H,s,OH), 6.41(1H,s), 6.74(1H,s,OH)

$^{13}$C-NMR (50 MHz) (d$_6$-DMSO) ppm: (internal standard TMS): 13.94(q), 21.05(t), 22.10(t), 28.75(t), 29.00-29.12(t×5), 29.61(t), 30.41(t), 31.33(t), 52.33(q, 52.68(q), 78.82(d), 79.55(s), 82.37(d), 166.95(s), 169.43(s), 174.44(s)

EXAMPLE 3

Preparation of Seco Acid of Cinatrin

A solution of Cinatrin A (4.9 mg, prepared as described in Example 1) in 1 ml of 0.5N NaOH was allowed to stand for 16 hours at room temperature. After washing with acetone, methanol, and distilled water, the reaction mixture was applied to CHP-20P 75-150$\mu$ column (Mitsubishi Chemical) previously equilibrated with 20% NaCl solution. The column was washed with 25 ml of 20% NaCl and developed with distilled water. The eluate was carefully examined for the existence of Cl$^-$ ion with silver nitrate. After the test became negative, about 15 ml of eluate was taken and purified using preparative HPLC (column: COSMOCIL 5C$_{18}$ 4.6$\phi$×150 mm) (Nakarai Tesk Inc.), solvent: 0.1% aqueous trifluoroacetic acid, acetonitrile=45:55, flow rate: 1 ml/min, detection: UV at 220 nm, retention time: 9.1 min (Cinatrin A) and 2.7 min (seco acid)). Fractions containing seco acid are concentrated and lyophylized to obtain 4.8 mg of seco acid Na salt.

Cinatrins B, C$_1$, C$_2$, and C$_3$ are also hydrolyzed in the same manner as above to obtain corresponding seco acids. The amount of each starting material and yield are listed below Table 3.

TABLE 3

Seco Acid Derivatives of Cinatrins

| Cinatrin | amount (mg) | seco acid Na salt (mg) |
|---|---|---|
| B | 4.9 | 5.7 |
| C$_1$ | 4.9 | 3.6* |
| C$_2$ | 9.3 | 7.3 |
| C$_3$ | 5.7 | 4.7* |

*seco acid of C$_1$ is the same as that of C$_3$

Retention times (min) of each Cinatrin and corresponding seco acid in the preparative HPLC of above are as follows:

| | Cinatrin | seco acid (min) |
|---|---|---|
| B | 14.7 | 3.5 |
| C$_1$ | 8.5 | 6.3 |
| C$_2$ | 9.3 | 4.6 |
| C$_3$ | 10.2 | 6.3 |

Figure 3A:
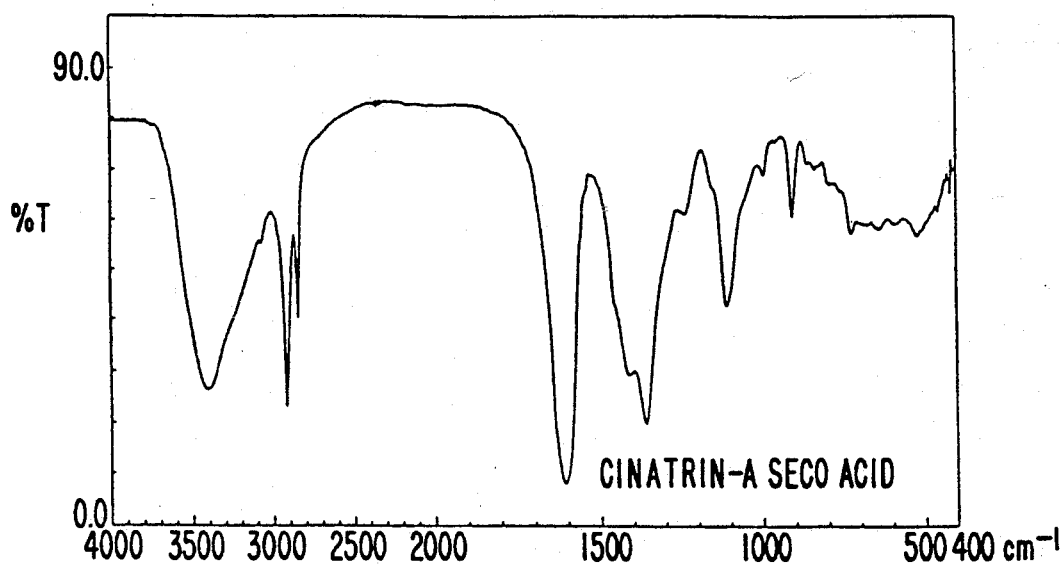
Figure 3B:
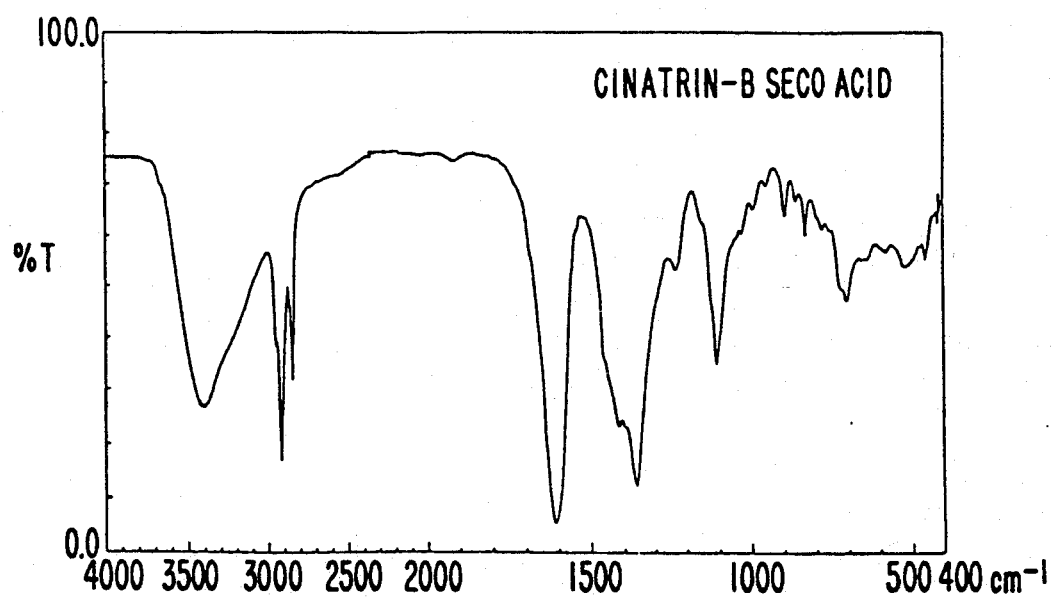
Figure 4A:
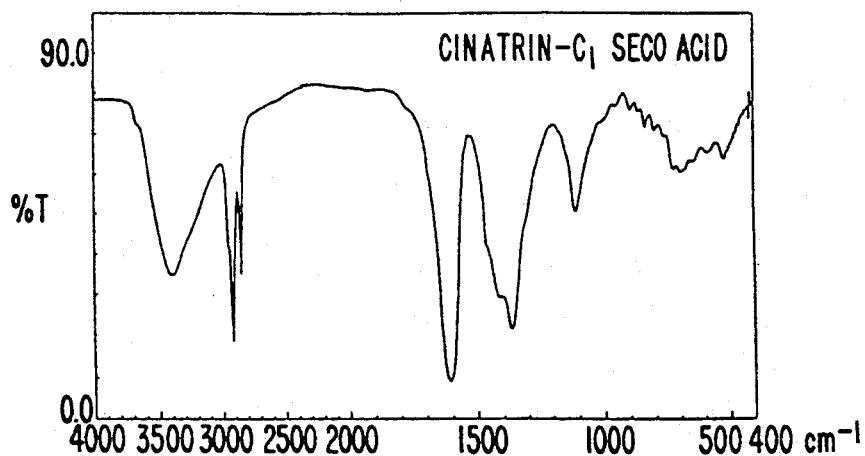
Figure 4B:
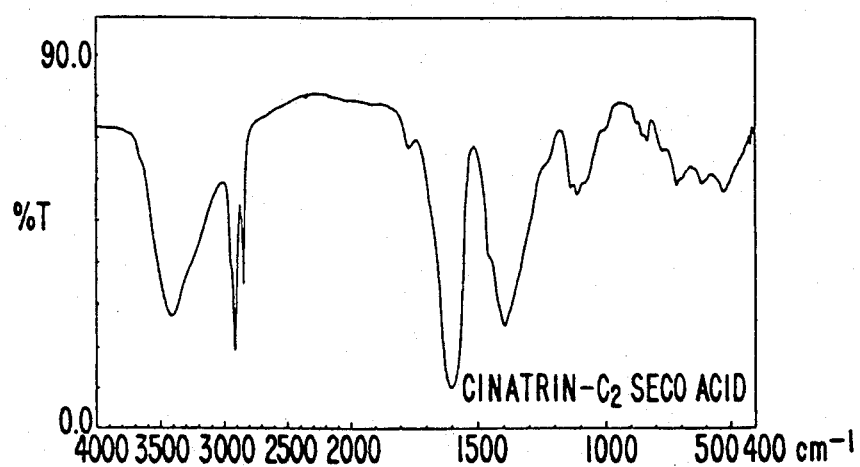
Figure 4C:
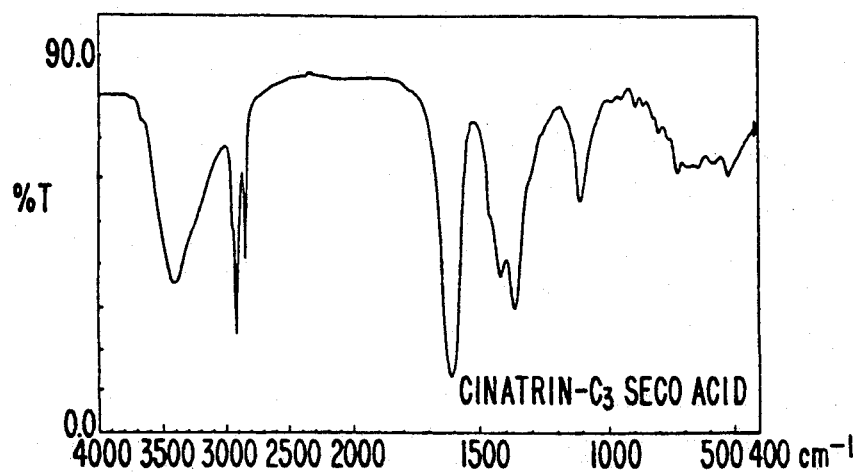

The data of IR spectrum of seco acid (Na) of Cinatrin are provided below and FIGS. 3 and 4.

| seco acid Na | IR (KBr) cm$^{-1}$ |
|---|---|
| Cinatrin A | 3408, 2918, 2848, 1609, 1415, 1362, 1235, 1111, 992, 906, 726, 639, 589, 522 |
| Cinatrin B | 3402, 2916, 2846, 1612, 1415, 1362, 1235, 1109, 896, 832, 780, 705, 578, 516 |
| Cinatrin C$_1$ | 3402, 2918, 2846, 1611, 1415, 1365, 1105, 720, 587, 519 |
| Cinatrin C$_2$ | 3412, 2918, 2848, 1601, 1399, 1114, 834, 718, 618, 527 |
| Cinatrin C$_3$ | 3410, 2918, 2846, 1613, 1417, 1363, 1105, 722, 586, 521 |

The SIMS data of each seco acid Na are listed below Table 4.

TABLE 4

| seco acid Na salt | Mol. formula | Mol. Weight | $[M - Na + 2H]^+$ (m/z) | $[M + H]^+$ (m/z) | $[M + Na]^+$ (m/z) |
|---|---|---|---|---|---|
| A | $C_{18}H_{27}O_{10}Na_3$ | 472 | 451 | 473 | 495 |
| B | $C_{18}H_{29}O_{10}Na_3$ | 474 | — | 475 | 497 |
| $C_1$ | $C_{18}H_{29}O_9Na_3$ | 458 | 437 | 459 | 481 |
| $C_2$ | $C_{18}H_{29}O_9Na_3$ | 458 | 437 | 459 | 481 |
| $C_3$ | $C_{18}H_{29}O_9Na_3$ | 458 | 437 | 459 | 481 |

Experiment 1

$PLA_2$ inhibitory activities of Cinatrin and its derivatives were determined according to the following procedure.

Method $PLA_2$ released from thrombin-stimulated rat platelets was prepared by immuno-affinity chromatography using antibody MD 7.1-coupled Sepharose (Murakami et. al, J. Biochem 104: 884-888, 1988). The standard assay conditions included, 250 μl of Tris-HCl buffer (100 mM, pH 7.4), $CaCl_2$ (3 mM), 40 μM [$^{14}$C]phosphatidylethanolamine and the enzyme. The reaction was started by the addition of the enzyme solution. Following incubation at 37° C. for 20 minutes, the reaction was terminated by addition of 1.25 ml of Dole's reagent (Dole, V. P. & H, Meinerts, J. Biol. Chem. 235: 2595-2599, 1960). Then released free fatty acid was extracted, and counted in Liquiflour (Du Pont-New England Nuclear) to determine the release of the radioactivity. Inhibition activity is expressed as percent of enzyme control.

Test Results

Concentration of active compounds required for exhibiting 50% inhibitory activity is shown below Table 5.

TABLE 5

| | $PLA_2$ Inhibitory Activity of Cinatrins ($IC_{50}$, μg/ml) | | |
|---|---|---|---|
| Cinatrin | lactone | methyl ester | seco acid (Na) |
| A | 117 | 83.2 | 56.2 |
| B | 54.9 | 83.2 | 30.9 |
| $C_1$ | >300 | 57.2 | 27.5 |
| $C_2$ | 300 | 300 | 17.5 |
| $C_3$ | 29.5 | 53.7 | 27.5 |

The above Table 5 shows that Cinatrin B and $C_3$ in lactone form are effective. It also shows the modification of lactones, that is, esterification or hydrolytic cleavage, can enhance the activity relatively. This means that more effective and less toxic $PLA_2$ inhibitor can be prepared through appropriate chemical modifications on Cinatrins of the invention.

$PLA_2$ inhibitory activity of Cinatrins is attributable to direct actions on $PLA_2$.

What is claimed is:

1. A process for the production of a compound of the formula

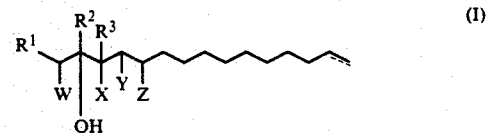

wherein $R^1$, $R^2$ and $R^3$ are —$COOR^4$, —$COOR^5$ and —$COOR^6$, respectively; $R^4$, $R^5$ and $R^6$ each is hydrogen, lower alkyl, or alkali metal; W is hydroxy; X, Y and Z each is hydrogen or hydroxyl; a dotted line indicates the presence or absence of a single bond; or where $W/R^3$, $X/R^1$ and/or $Z/R^3$ may be combined together, a lactone is formed which comprises cultivating *Circinotrichum falcatisporum* RF-641 or a variant thereof capable of producing said compound until substantial amount of said compound is produced, isolating the product from the culture, and, if desired, subjecting the compound to hydrolysis and/or esterification.

* * * * *